United States Patent
Joseph et al.

(10) Patent No.: US 9,682,932 B2
(45) Date of Patent: Jun. 20, 2017

(54) PROCESS FOR PRODUCTION OF HIGH PURITY BETA-CAROTENE AND LYCOPENE CRYSTALS FROM FUNGAL BIOMASS

(75) Inventors: Suresh Joseph, Tamil Nadu (IN); Arnaud Anandane, Puducherry (IN)

(73) Assignee: DYNADIS BIOTECH INDIA PRIVATE LIMITED, Puducherry (IN)

( * ) Notice: Subject to any disclaimer, the term of this patent is extended or adjusted under 35 U.S.C. 154(b) by 0 days.

(21) Appl. No.: 13/698,253

(22) PCT Filed: May 16, 2011

(86) PCT No.: PCT/IN2011/000343
§ 371 (c)(1),
(2), (4) Date: Nov. 15, 2012

(87) PCT Pub. No.: WO2011/145113
PCT Pub. Date: Nov. 24, 2011

(65) Prior Publication Data
US 2013/0066124 A1    Mar. 14, 2013

(30) Foreign Application Priority Data

May 17, 2010  (IN) .......................... 1380/CHE/2010

(51) Int. Cl.
C07C 403/24 (2006.01)
C12P 23/00 (2006.01)
C07C 11/02 (2006.01)

(52) U.S. Cl.
CPC ............ C07C 403/24 (2013.01); C07C 11/02 (2013.01); C12P 23/00 (2013.01)

(58) Field of Classification Search
None
See application file for complete search history.

(56) References Cited

U.S. PATENT DOCUMENTS

| | | | |
|---|---|---|---|
| 2,959,521 A | 11/1960 | Zajic et al. | |
| 3,268,606 A | 8/1966 | Jaeger et al. | |
| 5,714,658 A | 2/1998 | Heidlas et al. | |
| 5,858,700 A | 1/1999 | Ausich et al. | |
| 6,812,001 B2 | 11/2004 | Sibeijn et al. | |
| 7,015,014 B2 | 3/2006 | Schaap et al. | |
| 7,252,965 B2 | 8/2007 | Costa Perez et al. | |
| 7,799,540 B2 | 9/2010 | Rodriguez et al. | |
| 2002/0025548 A1 | 2/2002 | Sibeyn et al. | |
| 2002/0055135 A1 | 5/2002 | Sibeijn | |
| 2004/0067550 A1 | 4/2004 | Costa Perez et al. | |
| 2006/0105443 A1* | 5/2006 | Wu et al. .................... | 435/170 |
| 2010/0145116 A1 | 6/2010 | Van Keulen et al. | |

FOREIGN PATENT DOCUMENTS

| | | | |
|---|---|---|---|
| CN | 101870668 | | 1/2013 |
| EP | 0979302 | | 12/2009 |
| JP | 07298889 | A * | 11/1995 |
| WO | 98/03480 | | 1/1998 |
| WO | 98/50574 | | 11/1998 |
| WO | 01/55100 | | 8/2001 |
| WO | 01/83437 | | 11/2001 |
| WO | WO 03038064 | A2 * | 5/2003 |
| WO | 2008/108674 | | 9/2008 |

OTHER PUBLICATIONS

Sakamoto, Kazuchika. JP07298889A machine translation. Published 1995. p. 1-5.*
Cunningham RL et al. Hemicellulose Isolation from Annual Plants. Biotechnology and Bioengineering Symposium. 1986. No. 17. p. 159-168.*
English Abstract of CN 101870668 published Jan. 23, 2013.

* cited by examiner

*Primary Examiner* — Paul Holland
(74) *Attorney, Agent, or Firm* — Nevrivy Patent Law Group P.L.L.C.

(57) ABSTRACT

The present invention relates to a simple and economic method of extracting a crystalline Carotenoid compound, such as Beta-carotene, Lycopene, with a purity of at least 99%. The present invention further describes a process to prepare such a highly pure crystalline Carotenoid compound from microbial biomass, using an Anti-purity compound removal process followed by a mono-solvent extraction method. Further the process describes value addition of the co-products recovered during the extraction process thus resulting in a highly economical industrial method for the production of such high purity crystalline Carotenoids compound.

15 Claims, 1 Drawing Sheet

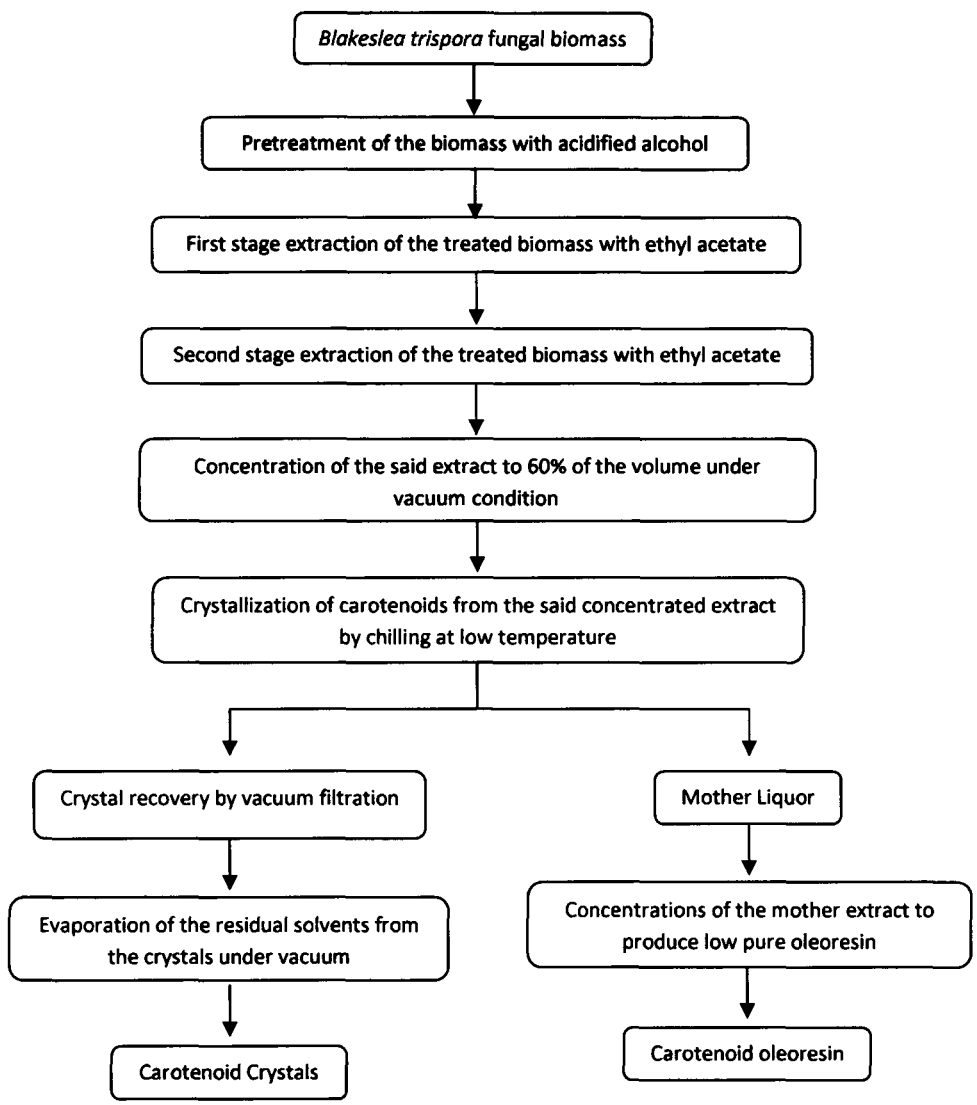

PROCESS FOR PRODUCTION OF HIGH PURITY BETA-CAROTENE AND LYCOPENE CRYSTALS FROM FUNGAL BIOMASS

FIELD OF INVENTION

The present invention relates to a field of microbially produced carotenoid compounds and it relates particularly to the method of extraction of carotenoid compounds such as beta carotene and Lycopene of high purity from fungal biomass and an optimised process of isolating carotenoid compounds of high purity.

BACKGROUND OF THE INVENTION

Carotenoids are the most widespread class of naturally occurring pigments in nature, present without exception in photosynthetic tissue and occurring with no definite pattern in non-photosynthetic tissues such as roots, flower petals, seeds and fruits. They are also found in algae, fungi, yeasts, molds, mushrooms and bacteria. They represent the most extended group of natural pigments that exists in nature. They are used in the industry as food supplements and colorants. They are known for their excellent anti-oxidant properties and as precursors of vitamin A.

Beta-carotene and Lycopene are important carotenoids used widely in Nutraceutical, Pharma, food and animal feed industries as natural antioxidants, functional colour and for food and feed fortification. High purity Carotenoid crystals plays a major role in the various formulations like encapsulation, water soluble powder or emulsion, high concentrate oil dispersion etc.

These high purity carotenoid crystals not only facilitate easier product formulation but also help to deliver high concentrated end products to meet the growing market demands of anti-oxidants and 'natural, colorants—a number of methods have been proposed and tried—to isolate and purify carotenoids and specifically Beta carotene.

Carotenoids and Beta carotene, in particular can be obtained from natural sources whether vegetal products such as tomato and carrot in which they are very small percentages or starting from cultures of selected algae, fungi etc. in which proportion of these components may increase.

Beta carotene obtained from fermentation broths of certain mucor fungi such as *Phycomyces; Blakeslea* etc. have certain advantages over the aforementioned natural sources. ie. 1. Elevated concentration of this compound with respect to the quantity of dry biomasses 2. Possible increase in production using 'enhanced carotenoid producing strains' obtained by classical mutagenesis/molecular biology techniques; optimisation of fermentation processes, use of "inducers,/'Inhibitors'.

For example: U.S. Pat. No. 2,959,521 describes enhanced production of beta carotene from fungi *Blakeslea trispora* in a culture medium containing Lecithin.

U.S. Pat. No. 7,799,540 Describes a process of producing lycopene through the fermentation of selected strains of *Blakeslea trispora* and extracting lycopene by a process of treating the fermented culture with alcohol and drying the biomass followed by a mechanical milling process to break the cell wall and the disrupted biomass is extracted by an organic solvent and the crystals are recovered by precipitation crystallization by addition of alcohol. The main disadvantage of this process is the mechanical milling method for cell disruption which might cause the loss of Lycopene;

U.S. Pat. No. 7,252,965 Discloses a method of production of Beta-carotene by fermentation of (+) and (−) strains of *Blakeslea trispora* followed by separation of the wet biomass and treatment with alcohol to dry the biomass for cell rupturing; then the ruptured cell biomass is subjected to solid-liquid extraction with an organic solvent and it is concentrated. Precipitation/crystallization—by adding alcohol thus a pure crystal of purity >95% is obtained. (Similar process is also explained in US application U.S. Pat. Application No. 20040067550) the disadvantage of this process is the mechanical disruption & drying of the biomass which might cause loss of beta-carotene and complexity of using multiple solvents for extraction and precipitation steps.

U.S. Pat. No. 7,015,014 (equivalent to WO 01/55100) teaches a method for the Isolation of Carotenoid crystals by microbial cell disruption to get an oily medium; this oily suspension is treated with water and the PH adjusted by adding alkali and further treated with alcohol or salt to get a filtrate containing beta-carotene crystals. This filtrate is subjected to several washing steps with multiple solvents followed by a separation and dryings step to get purified crystals. This process involves use of larger number of solvents and water media for the purification International patent application WO 03/038064 A2 describes method of producing lycopene by fermentation of mutated *Blakeslea trispora*. Lycopene crystals are extracted from the culture broth by means of cell disruption subsequent purification steps using organic solvents such as ethyl acetate, hexane and 1-butanol by adjusting the PH using alkali with optional addition of alcohol or acid to adjust the pH; this is further purified with organic solvent and washed with fresh solvent to give lycopene crystals. This process is highly complex, larger amount of solvents and reagents are used for the purification steps.

U.S. Pat. No. 6,812,001 (equitant to EP 0979302 & WO 01/83437 A1) Describes a method to obtain carotenoid crystals from microbial biomass, the method involves cell wall disruption by homogenization and followed by lipid removal by alcohol treatment. The crystals from the cellular debris is collected by floating in water. According to this method ether salt or oil can be used in the place of water to float crystals, the yield thus obtained is 35% only.

WO 98/50574 Teaches a method of isolating carotenoid crystals from microbial biomass which involves disrupting the microbial cell walls, removing the cellular debris from the resulting carotenoid crystal containing residue. Further solvent added to remove lipid. Then Carotenoids are extracted using ethyl acetate, hexane or oil followed by several purification & washing steps which requires more solvent & water in the process, thus the crystals purity of 93.3% is achieved with an yield of 35% only.

U.S. Pat. No. 5,858,700 Teaches a process for the purification of lycopene crystals by saponifying lycopene containing oleoresin using propylene glycol, alkali and water to recover the crystals U.S. Pat. No. 5,714,658, Describes a process for the extraction of carotenes from natural sources using a mixture of an acetic acid ester (ethyl acetate or butyl acetate or in combination), and with an edible oil.

U.S. Pat. No. 3,268,606 Describes a process of extracting beta-carotene from fungal biomass by treating the fermented mycelium with alcohol to remove the moisture and extracting the dried mycelium with ethylene chloride or Benzene in several steps to yield a filtrate rich in beta-carotene. This filtrate is further concentrated and subjected to crystallization with acetone and absolute alcohol to recover the high purity beta-carotene crystals. The disadvantage of this process is the complexity in industrial application, usage of toxic solvents like benzene.

U.S. Pat. Application No. 20020025548 (equivalent to WO/1998/003480) discloses a method to extract beta carotene from natural sources by direct extraction with organic solvents, vegetable oils or supercritical fluids, followed by crystallization or precipitation and washing of the crystals with an anti-solvent.

U.S. Pat. Application No. 20060105443 explains a method to isolate lycopene from transformed or naturally derived bacterial cells; the steps in the process comprises: isolating a biomass from a fermented broth; treating the isolated biomass with alcohol; extracting the lycopene from the alcohol treated biomass with methylene chloride; solid mixture is removed and the filtrate is vacuum contracted; the concentrates suspension is washed with acetone to recover lycopene crystals.

U.S. Pat. Application No. 20060234333 (equivalent to WO/2004/063359) discloses a method for producing carotenoids or their precursors using genetically modified organisms of the *blakeslea* genus. The process involves recovery of biomass from the medium and washing the same with water. Biomass is sterilized and cell disruptions are carried out using steam or microwave radiation followed by extraction using solvents such as dichloromethane or supercritical carbon dioxide or tetrahydrofuran. The filtrate obtained after the extraction is subjected to crystallization step using a carotenoid non soluble solvent.

CN101870668 Discloses a method for preparing beta-carotene from *Blakeslea trispora* through fermentation & drying the biomass and milling and pulverizing the dry mycelia, followed by solvent extraction using dichloromethane. The major disadvantage of this process is mechanical cell disruption using milling and pulverizing which will lead to loss of beta-carotene.

U.S. Pat. Application No. 20100145116 (equivalent to WO/2008/108674) Describes a process for the production and extraction of Carotenoids without cell disruption by direct solid liquid extraction using a ketone and alcohol (acetone and ethanol or acetone and methanol) followed by a second extraction using a mixture of hydrophobic solvents (hexane and tert-butylmethyl ethe) and finally crystallization. The major disadvantage of the process is using more number of solvents, multiple extraction steps and complicated process.

It is clearly evident that the prior art that the disclosed processes involve: different types & large amount of Organic solvents for the extraction of substantially pure crystals of beta-carotene or lycopene, and the methods are complicated. In most of the cases the purity of the final product is below expectation. The processes for obtaining Beta carotene from fermentation broths described until present generally imply an extraction stage and successive crystallizations and re-crystallizations and even stages of Chromatographic purifications requiring high consumption of solvents. Hence there is a need for a simple, cost effective and industrially viable method for extraction.

OBJECTS AND SUMMARY OF THE INVENTION

An object of the invention is to provide a simple and cost effective method for extracting Carotenoids such a beta-carotene and lycopene from fungal biomass Another object of the invention is to provide a simple mono-solvent extraction process of recovering substantially pure Carotenoids crystals, where purity is almost 99% without use of further process of purifying with water or adding any other solvents.

Yet another object of this invention is to provide a process with value addition—ie. a process which yields important and commercially useful by-products.

The present invention disclosed a process for production of beta-carotene and lycopene crystals with a purity of minimum 99% from natural sources, especially from fungal biomass produced by the fermentation of *Blakeslea trispora* to give ready biomass containing carotenoids such as beta-carotene and lycopene. The process comprises of the following steps.

a) Pretreatment of the biomass with acidified alcohol to remove free oils, sugars and other soluble impurities in the biomass and also to increase the cellular porosity for better extraction of carotenoids.

b) Two stage extraction of the treated biomass with a mono solvent like ethyl acetate. The initial extraction is with a solvent ratio of 20 times and the second extraction with 10 times ratio of solvent.

c) Further concentration of the said extract to 60% of the volume under vacuum condition.

d) Crystallization of beta-carotene or lycopene from the said concentrated extract by chilling at low temperature.

e) Crystal recovery is done by vacuum filtration.

f) Vacuum evaporation of the filtrate from the above step to recover the residue solvent.

The concentrations of the mother extract yields a carotenoid rich oleoresin containing Beta-carotene or lycopene respectively.

The overall yield of the process is ≥87%.

In a preferred embodiment, the method provides beta-carotene or lycopene crystals from a natural source with a purity of ≥99% and byproduct of low purity oleoresin-which is further treated with the spent biomass & the residue of the pretreatment step, to give an animal feed mixture

DETAILED DESCRIPTION OF THE INVENTION

The present invention discloses a process for the production of crystalline Carotenoid with a purity of at least 99%, most preferably 99.9% by a mono-solvent, simple, efficient and highly Cost effective & economically viable industrial extraction process. The extraction efficiency and the purity of the crystals are improved by a pretreatment process acidified ethanol under homogenization at a low temperature.

The acidified ethanol is made out of treating acetic acid or any other acids to the said alcohol at the ratio lower than 4.5% (w/w), preferably lower than 3.5% (w/w), more preferably lower than 2.5% (w/w), most preferably lower than 2.2% (w/w).

The Process of the Invention Comprises the Following Steps:

Carotenoids containing biomass preferably from Fungi *Blakeslea trispora* is subjected to pretreatment & cellular disruption by mild acidified alcohol treatment, whereas the acid is mild acetic acid and alcohol is ethanol, under homogenization to remove the anti-purity compounds such as free oils, proteins, mineral, carbohydrates, and to increase the cellular porosity to an extend to increasing the efficiency of the extraction process.

Then the pretreated biomass is subjected to mechanical separation to recover the solid biomass for further processing. The filtrate is collected and stored for further processing.

Next step involves a solid liquid extraction using an organic solvent, preferably ethyl acetate at a ratio of 15-40 times, preferably 15-30 times, more preferably 18-25 times, and most preferably 19-22 times. Extraction was carried out at a temperature of about 40° C. to 80° C., more preferably 45° C. to 75° C. and most preferably 48° C. to 60° C.

The extracted mixture is filtered mechanically to separate the mother liquor containing the carotenoid crystals and the spent biomass. The spent biomass is further subjected to a secondary extraction (repeat extraction) with the same organic solvent, ethyl acetate at a ratio of 5-20 times, preferably 7-18 times, more preferably 8-15 times, and most preferably 8.5-12.5 times. Where the extraction was carried out at a temperature of about 40° C. to 80° C., more preferably 45° C. to 75° C. and most preferably 48° C. to 60° C.

The second extracted mixture is filtered mechanically to recover the Mother liquor and the spent biomass, thus the mother liquor collected from the two extraction steps are pooled together to get a homogenous mixture of extracted carotenoids containing suspension.

This is followed by a chilling crystallization method to recover the crystals the chilling temperature is from −5° C. to 10° C., preferably −3° C. to 8° C., more preferably −2.5° C. to 6.5° C., and most preferably −1° C. to 5° C.

The chilled suspension is filtered using high efficient mechanical filter under vacuum to get high purity Beta-carotene or Lycopene crystals.

Finally the recovered crystals are subjected to vacuum drying to remove the remaining solvent traces from the wet crystals, resulting in solvent free high purity Beta-carotene or Lycopene crystals.

The spent mother liquor with traces of carotenoid are concentrated further to produce oleoresin with 1-5% Beta-carotene or Lycopene, preferably 1.5-4.5%, more preferable 1.6 to 4.0% and most preferably 1.7 to 3.9%, The oleoresin, spent biomass and residue from the first step pretreatment are blended along with ingredients like filler, binders and further extruded to produce value added pellets for animal feed application and other application. The fillers like cellulose, dextrin, gums etc are used and the binder such as cellulose based, starch based, etc are used.

EXAMPLES 1

50 gms of *Blakeslea trispora* biomass containing 62.20 gms/kg of beta-carotene is loaded into 0.5 liter capacity round bottomed flask with an agitator, To this 150 ml of acidified ethanol with 2% acetic acid in ethanol is added at room temperature of 35 deg C., then this mixture is stirred for 30 min. Once the treatment is completed, the treated mixture is vacuum filtered to yield 53.4 Gms of biomass. Then the treated biomass is transferred into 5 liter capacity round bottomed flask, to which 1000 ml of ethyl acetate is added. This mixture is homogenized for an hour under stirring at a temperature of about 50 deg C. in hot water bath system. After one hour, the mixture is vacuum filtered to give 47.3 gms of extracted biomass and 980 ml of Mother liquor. The Mother liquor is kept stored for further beta-carotene recovery. Then the extracted biomass is taken for second extraction with 500 ml of ethyl acetate at the same conditions like the first extraction. After second extraction, 426 ml of Mother liquor and 47.2 gms of spent biomass were recovered. The spent biomass is further treated and used for feed application. The Mother liquor from both the first and second extraction were pooled in 2000 ml round bottomed flask and concentrated till 60% of the volume and then chilled at 5 deg C. in cold water bath for an hour's time for the crystallization of betacarotene. After chilling, the mother liquor is vacuum filtration to recover crystals and then dried under vacuum, obtaining 2.16 gms of betacarotene crystals with a spectrophotometric purity of 99.30%. The filtered mother liquor is completely distilled under vacuum to recover 15.23 gms of betacarotene oleoresin with a spectrophotometric purity of 1.16%. In this process the total yield is about 89.96%.

EXAMPLES 2

50 gms of *Blakeslea trispora* biomass containing 62.20 gms/kg of beta-carotene is loaded into 0.5 liter capacity round bottomed flask with an agitator, To this 150 ml of acidified ethanol with 2% acetic acid in ethanol is added at room temperature of 35 deg C., then this mixture is stirred for 30 min. Once the reaction is completed, the reaction mixture is vacuum filtered to yield 51.2 Gms of treated biomass. Then the treated biomass is then transferred into 5 liter capacity round bottomed flask, to which 1000 ml of ethyl acetate is added. This mixture is homogenized for an hour under stirring at a temperature of about 50 deg C. in hot water bath system. After one hour, the mixture is vacuum filtered to give 49.1 gms of extracted biomass and 988 ml of Mother liquor. The Mother liquor is stored for further beta-carotene recovery. Then the extracted biomass is taken for second extraction with 500 ml of ethyl acetate at the same conditions like the first extraction. After second extraction, 442 ml of Mother Liquor and 49.1 gms of spent biomass were recovered. The spent biomass is further treated and used for feed application. The Mother liquor from both the first and second extraction were pooled in 2000 ml round bottomed flask, without concentration the mixture is chilled at 5 deg C. in cold water bath for an hour's time for the crystallization of beta-carotene. After chilling, the mother liquor is vacuum filtration to recover crystals and then dried under vacuum, obtaining 2.53 gms of beta-carotene crystals with a spectrophotometric purity of 99.01%. The filtered mother liquor is completely distilled under vacuum to recover 10.23 gms of beta-carotene oleoresin with a spectrophotometric purity of 2.16%. In this process the total yield is about 79.68%.

EXAMPLES 3

500 gms of *Blakeslea trispora* biomass containing 62.20 gms/kg of beta-carotene is loaded into 5.0 liter capacity round bottomed flask with an agitator, To this 1500 ml of acidified ethanol with 2% acetic acid in ethanol is added at room temperature of 35 deg C., then this mixture is stirred for 30 min. Once the reaction is completed, the reaction mixture is vacuum filtered to yield 518.0 Gms of treated biomass. Then the treated biomass is then loaded into 15 liter capacity round bottomed flask, to which 10000 ml of ethyl acetate is added. This mixture is homogenized for an hour under stirring at a temperature of about 50 deg C. in hot water bath system. After one hour, the mixture is vacuum filtered to give 494.0 gms of extracted biomass and 9100 ml of Mother liquor. The Mother liquor is stored for further beta-carotene recovery. Then the extracted biomass is taken for second extraction with 5000 ml of ethyl acetate at the same conditions like the first extraction. After second extraction, 4400 ml of Mother Liquor and 494 gms of spent biomass were recovered. The spent biomass is further treated and used for feed application. The Mother liquor from both the first and second extraction were pooled in 20 liter round bottomed flask and concentrated till 60% of the volume and then chilled at 5 deg C. in cold water bath for an hour's time for the crystallization of beta-carotene. After chilling, the mother liquor is vacuum filtration to recover crystals and then dried under vacuum, obtaining 25.731 gms of beta-carotene crystals with a spectrophotometric purity of 99.07%. The filtered mother liquor is completely distilled under vacuum to recover 173.24 gms of beta-carotene oleoresin with a spectrophotometric purity of 1.46%. In this process the total yield is about 90.10%.

EXAMPLES 4

5.0 kg of *Blakeslea trispora* biomass containing 62.20 gms/kg of beta-carotene is loaded into 150 liter capacity pilot plant with an agitator, To this 15 liter of acidified ethanol with 2% acetic acid in ethanol is added at room temperature of 35 deg C., then this mixture is stirred for 30 min. Once the reaction is completed, the reaction mixture is centrifuged to yield 5.24 kg of treated biomass. Then the treated biomass is then loaded into 150 liter capacity pilot plant, to which 100 liter of ethyl acetate is added. This mixture is homogenized for an hour under stirring at a temperature of about 50 deg C. in hot water bath system. After one hour, the mixture is vacuum filtered to give 4.84 kg of extracted biomass and 91 liter of Mother Liquor. The Mother liquor is stored for further beta-carotene recovery. Then the extracted biomass is taken for second extraction with 50 liter of ethyl acetate at the same conditions like the first extraction. After second extraction, 42 liter of Mother liquor and 5.12 kg of spent biomass were recovered. The spent biomass is further treated and used for feed application. The Mother liquor from both the first and second extraction were pooled in 200 liter round bottomed flask and concentrated till 60% of the volume and then chilled at 5 deg C. in cold water bath for an hour's time for the crystallization of beta-carotene. After chilling, the mother liquor is vacuum filtration to recover crystals and then dried under vacuum, obtaining 245.8 gms of beta-carotene crystals with a spectrophotometric purity of 99.34%. The filtered mother liquor is completely distilled under vacuum to recover 1473.32 gms of beta-carotene oleoresin with a spectrophotometric purity of 2.09%. In this process the total yield is about 88.41%.

EXAMPLE 5

500 gms of *Blakeslea trispora* biomass containing 37.20 gms/kg of Lycopene is loaded into 5.0 liter capacity round bottomed flask with an agitator, To this 1500 ml of acidified ethanol with 2% acetic acid in ethanol is added at room temperature of 35 deg C., then this mixture is stirred for 30 min. Once the reaction is completed, the reaction mixture is vacuum filtered to yield 481.0 Gms of treated biomass. Then the treated biomass is then loaded into 15 liter capacity round bottomed flask, to which 10000 ml of ethyl acetate is added. This mixture is homogenized for an hour under stirring at a temperature of about 50 deg C. in hot water bath system. After one hour, the mixture is vacuum filtered to give 442.0 gms of extracted biomass and 9100 ml of Mother liquor. The Mother liquor is stored for further beta-carotene recovery. Then the extracted biomass is taken for second extraction with 5000 ml of ethyl acetate at the same conditions like the first extraction. After second extraction, 4600 ml of Mother Liquor and 464 gms of spent biomass were recovered. The spent biomass is further treated and used for feed application. The Mother liquor from both the first and second extraction were pooled in 20 liter round bottomed flask and concentrated till 60% of the volume and then chilled at 5 deg C. in cold water bath for an hour's time for the crystallization of Lycopene. After chilling, the mother liquor is vacuum filtration to recover crystals and then dried under vacuum, obtaining 15.55 gms of lycopene crystals with a spectrophotometric purity of 99.85%. The filtered mother liquor is completely distilled under vacuum to recover 30.5 gms of beta-carotene oleoresin with a spectrophotometric purity of 2.90%. In this process the total yield is about 88.23%.

The present invention discloses a production of crystalline Carotenoid with very high purity; purity of almost 99% or more, most preferably 99.9% by a mono-solvent simple, efficient and economical extraction process. The extraction efficiency and the purity of the crystals are improved by a pretreatment process of acetic acid acidified ethanol under homogenization at a low temperature.

The acidified ethanol, is meant an amount of acetic acid or other acids in the solvent of lower than 4.5% (w/w), preferably lower than 3.5% (w/w), more preferably lower than 2.5% (w/w), most preferably lower than 2.2% (w/w).

The process of the invention: Example: (a) Disintegration of carotenoid-containing biomass, preferably from Fungi spp. Including *Blakeslea* by mild acidified alcohol treatment, whereas the acid is mild acetic acid and alcohol is ethanol, under homogenization to remove the anti-purity compounds such as free oils, proteins, mineral, carbohydrates, etc., to an extend to increasing the efficiency of the process.

(b) Mechanical separation of the treated biomass to recover the solid biomass for further processing.

(c) The treated biomass is then extraction with an organic solvent, preferably ethyl acetate at a ratio of 15-40 times, preferably 15-30 times, more preferably 18-25 times, and most preferably 19-22 times.

(d) The extracted mixture is filtered mechanically to recover the Mother liquor and the spent biomass.

(e) The spent biomass is extracted for the second time with the same organic solvent, ethyl acetate at a ratio of 5-20 times, preferably 7-18 times, more preferably 8-15 times, and most preferably 8.5-12.5 times.

(f) The second extracted mixture is filtered mechanically to recover the Mother liquor and the spent biomass (g) The high pure crystals are recovered from the pooled mother liquor of both the extraction under chilling condition, the chilling temperature is from −5° C. to 10° C., preferably −3° C. to 8° C., more preferably −2.5° C. to 6.5° C., and most preferably −1° C. to 5° C.

(h) The high pure crystals of carotenoid are recovered by the mechanical separator.

(i) The solvent traces are removed from the isolated crystal by vacuum drying to give solvent free high purity crystals.

(j) The spent mother liquor with traces of carotenoid are concentrated further to produce oleoresin with 1-5% Carotenoid, preferably 1.5-4.5%, more preferable 1.6 to 4.0% and most preferably 1.7 to 3.9%, (k) The oleoresin, spent biomass and residue from the pretreatment are blended along with ingredients like filler, binders and further extruded to produce value added pellets for animal feed application and other application. The fillers like cellulose, dextrin, gums etc are used and the binder such as cellulose based, starch based, etc are used. The foregoing description is to be considered as illustrative only and not meant to limit the scope of the invention.

We claim:

1. A method of extraction of carotenoids having 99% and above purity from fungal biomass, said method comprising the steps of:
   a) pre-treatment and cellular disruption of carotenoid-containing fungal biomass with acidified alcohol to obtain a treated fungal biomass;
   b) separating said treated fungal biomass from step a) mechanically to obtain a solid fungal biomass;
   c) extracting said solid fungal biomass from step b) with an organic solvent to obtain an extracted mixture comprising beta-carotene and/or lycopene;
   d) filtering said extracted mixture from step c) to recover a mother liquor containing carotenoid crystals and fungal biomass;
   e) repeating said extracting step (c) with an organic solvent to obtain a second extracted mixture;
   f) filtering said second extracted mixture from step (e) to recover a mother liquor and fungal biomass;
   g) combining and recovering pure crystals from said mother liquors obtained from steps d) and f) by crystallization at a temperature of −5° C. to 10° C. to obtain a chilled suspension and a mother liquor;
   h) filtering said chilled suspension from step g) to obtain beta-carotene or lycopene crystals with a purity greater than, or equal to, 99%; and
   i) concentrating said mother liquor from step g) containing traces of carotenoid to produce oleoresin comprising beta-carotene or lycopene.

2. The method of extraction of claim 1, wherein said purity of said beta-carotene crystals is 99% or more.

3. The method of extraction of claim 1, wherein said purity of said lycopene crystals is 99.9%.

4. The method of extraction of claim 1, wherein said carotenoid containing fungal biomass is *Blakeslea* sp.

5. The method of extraction of claim 4, wherein said fungal biomass is *Blakeslea trispora*.

6. The method of extraction of claim 1, wherein acidified alcohol comprises an acid to alcohol ratio lower than 4.5% (w/w), lower than 3.5% (w/w), lower than 2.5% (w/w) or lower than 2.2% (w/w).

7. The method of extraction of claim 6, wherein said acidified alcohol consists of ethanol and acetic acid.

8. The method of extraction of claim 1, wherein said organic solvent for extraction in step c) is ethyl acetate.

9. The method of extraction of claim 8, wherein said ethyl acetate is present at a solid to liquid ratio of 15 to 40 times, 15 to 30 times, 18 to 25 times, or 19 to 22 times.

10. The method of extraction of claim 1, wherein said organic solvent for extraction in step e) is ethyl acetate at a solid to liquid ratio of 5 to 20 times, 7 to 18 times, 8 to 15 times, or 8.5 to 12.5 times.

11. The method of extraction of claim 1, wherein said extracting of steps c) and e) is carried out at a temperature of 40° C. to 80° C., 45° C. to 75° C. or 48° C. to 60° C.

12. The method of extraction of claim 10, wherein said extracting of step e) is carried out at a temperature of 40° C. to 80° C., 45° C. to 75° C. or 48° C. to 60° C.

13. The method of extraction of claim 1, wherein said crystallization of step g) is carried out at a temperature from 3° C. to 8° C., −2.5° C. to 6.5° C., or −1° C. to 5° C.

14. The method of extraction of claim 1, wherein said filtering of step h) is performed using a mechanical filter under vacuum and vacuum drying.

15. The method of extraction of claim 1, wherein said oleoresin of step i) comprises an amount of beta carotene or lycopene selected from the group consisting of 1 to 5%, 1.5% to 4.5%, 1.6 to 4.0% and 1.7 to 3.9%.

* * * * *